US00PP23181P2

(12) United States Plant Patent
Hurd

(10) Patent No.: US PP23,181 P2
(45) Date of Patent: Nov. 13, 2012

(54) ***LEUCANTHEMUM* PLANT NAMED 'BANANA CREAM'**

(50) Latin Name: ***Leucanthemum×superbum* (L. Burbank)**
Varietal Denomination: Banana Cream

(75) Inventor: Kevin A. Hurd, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 319 days.

(21) Appl. No.: 12/799,115

(22) Filed: Apr. 19, 2010

(51) Int. Cl.
*A01H 5/00* (2006.01)

(52) U.S. Cl. ..... Plt./285

(58) Field of Classification Search ..... Plt./285
See application file for complete search history.

(56) References Cited

U.S. PATENT DOCUMENTS

| | | | | |
|---|---|---|---|---|
| PP12,837 | P2 * | 8/2002 | van Noort | Plt./285 |
| PP15,204 | P2 * | 10/2004 | Kaliebe | Plt./285 |
| PP19,242 | P2 * | 9/2008 | Mehring-Lemper | Plt./263.1 |
| PP22,654 | P2 * | 4/2012 | Korlipara | Plt./285 |

OTHER PUBLICATIONS

UPOV ROM GTITM Computer Database, GTI Jouve Retrieval Software 2011/04 Citation for 'Banana Cream'.*
"*Leucanthemum superbum* 'Banana Cream' PPAF CPBRAF" available at http://www.perennialresource.com accessed Sep. 30, 2011.*
PLUTO: Plant Variety Database CN Citation for 'Banana Cream'.*

* cited by examiner

*Primary Examiner* — Wendy C Haas

(57) ABSTRACT

The new Shasta Daisy plant, *Leucanthemum* 'Banana Cream', is a sturdy plant with dark green serrated foliage, strong heavily-branched stems, and flowering with large terminal heads and numerous axillary heads having ray petals starting off light lemon yellow and brightening to near white. The new plant is useful for long-flowering attractive landscaping in borders, in mass, as accent plants, containerized for patio or indoor use, or as a cut flower.

1 Drawing Sheet

Botanical classification: *Leucanthemum×superbum* (L. Burbank).
Variety denomination: 'Banana Cream'.

BACKGROUND OF THE INVENTION

The original Shasta Daisies were bred by Luther Burbank in the late 1800's as a cross between *Leucanthemum maximum* (Ramond) DC. with *Leucanthemum lacustre* (Broth.) Samp. The new plant, *Leucanthemum* 'Banana Cream' originated from a planned cross-pollination made by the inventor, Kevin A. Hurd, at a nursery in Zeeland, Mich., USA in the summer of 2006. The new *Leucanthemum* was originally given the breeder number 06-12-10 as a cross between *Leucanthemum×superbum* 'Leumayel' U.S. Plant Pat. No. 19,242 as the female or seed parent and *Leucanthemum× superbum* 'Sunny Side Up' U.S. Plant Pat. No. 12,837 as the male or pollen parent and was selected for further evaluation by the Inventor in the trial fields of the same nursery in Zeeland, Mich. in the summer of 2008. The present invention relates to a new and distinct cultivar of Shasta Daisy botanically known as *Leucanthemum×superbum* and hereinafter referred to by the cultivar name 'Banana Cream'.

Asexual reproduction of the new cultivar by stem tip cuttings and shoot tip plant tissue culture at the same nursery in Zeeland, Mich. has demonstrated that the new cultivar reproduces true to type with all of the characteristics of the original plant retained through successive generations of asexual propagation.

BRIEF SUMMARY OF THE INVENTION

The new plant, *Leucanthemum* 'Banana Cream', is most closely compared to the female parent, *Leucanthemum* 'Leumayel' U.S. Plant Pat. No. 19,242, more commonly referred to in the trade as *Leucanthemum* 'Broadway Lights'. In test trials in Zeeland, Mich. the new plant, 'Banana Cream', had significantly more axillary branches and flowers than 'Leumayel' giving a much longer season of effective bloom. Terminal flowers of 'Banana Cream' are about 10% larger than the terminal flowers of 'Leumayel'.

'Banana Cream' differs from its male parent in having more yellow ray petals compared to the white ray petals of 'Sunny Side Up'.

*Leucanthemum* 'Banana Cream' differs from all cultivars known to the inventor in the following combined traits:

1. Sturdy plants with dark green serrated foliage.
2. Strong heavily-branched stems.
3. Flowering with large terminal heads and numerous axillary heads.
4. Single row of ray petals starting off light lemon yellow and brightening to near white.

BRIEF DESCRIPTION OF THE PHOTOGRAPHS

The photographs of the new plant demonstrate the overall appearance and landscape qualities of the new plant, including the unique traits. The colors are as accurate as reasonably possible with color reproductions. Ambient light spectrum, source, direction and temperature may cause the appearance of minor variation in color.

DETAILED BOTANICAL DESCRIPTION

Figure 1:
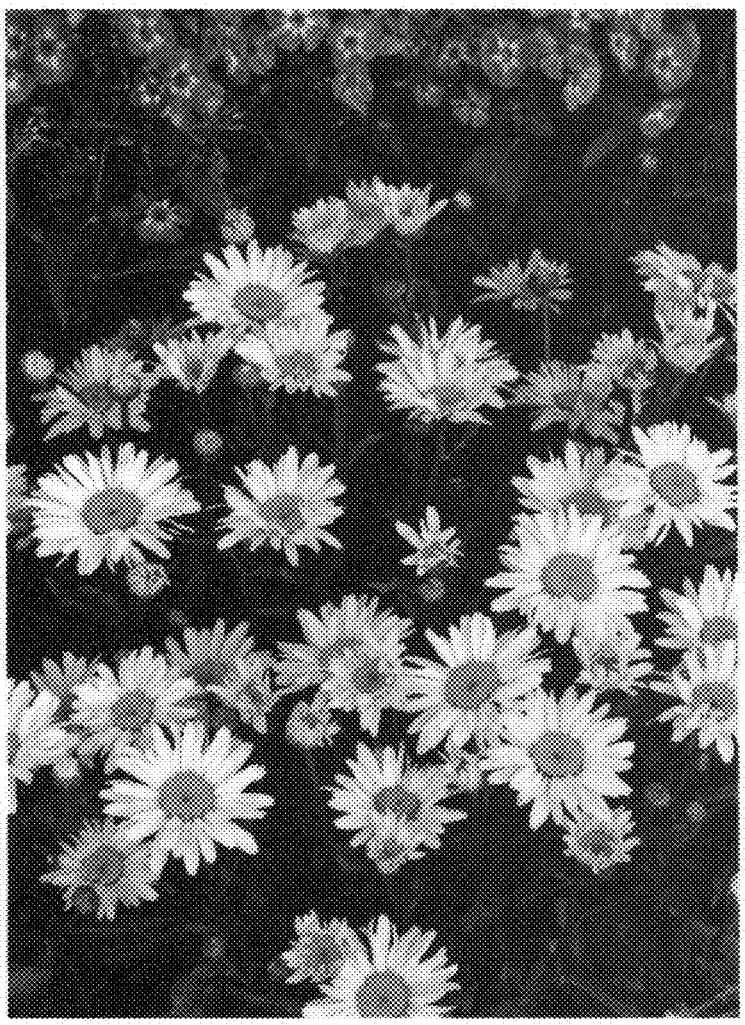
FIG. 1 Shows the new plant flowering in a landscape setting.
Figure 2:
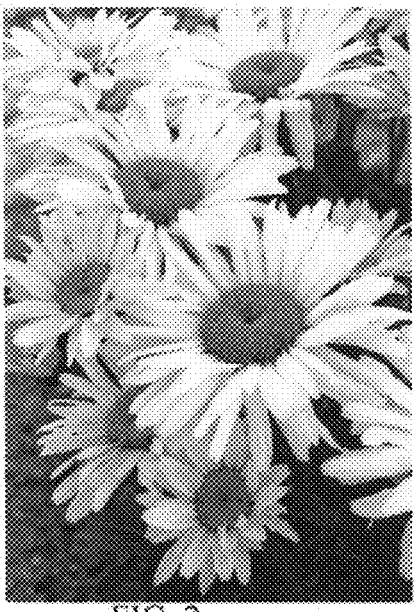
FIG. 2 Shows a close-up of the flowers and the change in ray petal color.

The following descriptions and color references are based on the 2001 edition of The Royal Horticultural Society Colour Chart except where common dictionary terms are used. The new plant has not been observed in all possible environments and conditions. The phenotype of 'Banana Cream' may vary between growing conditions such as changes in temperature, light intensity, water availability, fertility, but without change in the genotype.

Trial plants of about 9 months of age were grown in Zeeland, Mich. in a full-sun, loamy-sand trial field environment with supplemental water and fertilizer as needed. Summer temperatures range from night lows of about 10° C. to daytime highs of about 32° C. Measurements and numerical values represent averages of trial plants.

Botanical classification: *Leucanthemum×superbum* (L. Burbank).

Parentage: Female parent *Leucanthemum×superbum* 'Leumayel' U.S. Plant Pat. No. 19,242. Male parent *Leucanthemum×superbum* 'Sunny Side Up' U.S. Plant Pat. No. 12,837.

Habit: Herbaceous perennial with multiple branched stems arising from rhizome base; about 50 cm tall and 25 cm across with rounded top and nearly vertical sides.

Roots: Fibrous, thin, heavily branched.

Propagation: Tip cuttings or tissue culture; about two weeks to produce roots from cutting; about 33 weeks to finish to flower in 3.8 liter pot depending on season.

Stems: 4 to 5 main stems per plant, strong, upright, 8 mm diameter at base, 50 cm tall; canaliculated, hispidulous; coloration between RHS 139A and RHS 138B, with sun exposure at base coloration nearest RHS N186C.

Axillary branches: 5 to 13 per main stem, between 7 to 20 cm long and 4 mm diameter; less canaliculated than main stem, hispidulous; at angles of about 20° from vertical becoming vertical; coloration between RHS 139A and RHS 138B.

Leaves: Serrated, glabrous above, glabrous below except for main veins hispidulous, dentate with about ten teeth between 2 and 4 mm long; apex acute; base sessile to attenuate, partially clasping; lowest leaves about 22 cm long and 4.5 cm wide, distal leaves 6 cm long and 1 cm wide; adaxial coloration RHS 139A, abaxial coloration RHS 1378; fragrance none detected.

Veins: Major veins anastomosing, slightly recessed, same color as surrounding leaf on abaxial side, coloration nearest RHS 138B on adaxial side; center vein to 2.5 mm across with coloration of RHS 139D on both sides.

Flowers: Capitate, 24 to 30 per plant; primary flowers 14 cm across to 1.5 cm tall, axillary flowers 10 cm across and 1.2 cm tall; comprising about 50 ray florets and 800 disc florets; individual lasting about three weeks on or cut from plant; fragrant with age slightly offensive.

Flowering period: Early summer to fall.

Peduncle: Strong, hispidulous, round to canaliculate but less canaliculate than stem, 6 to 20 cm long and 2 to 3 mm diameter.

Bud: With petals still vertical, adaxial coloration between RHS 4A and RHS 4B and abaxial coloration nearest RHS 4C.

Ray florets: Arranged around perimeter of capitulum; 52 cm long and 7 mm wide, lanceolate, glabrous, acute apex having one to three clefts with center cleft 2 mm deep and two others on either side about 1 mm deep; base attenuate.

Ray floret color: As petals are first at 180° horizontal adaxial RHS 4C and abaxial RHS 4D; mature flower adaxial nearest RHS 155D and abaxial lighter than RHS 155D except apical 2 mm of RHS 4D; base 7 to 8mm on adaxial side and S mm on abaxial side RHS 143B.

Disc florets: About 800 per inflorescence in center of capitulum, combined 3.5 cm across and 1.2 cm tall; individual floret 1.0 cm tall and 2.5 mm wide, five tepals 3 mm long with acute apex, fused at base.

Disc floret color: Base between RHS 143 C and RHS 143D; apical 3 mm of tepals RHS 14B.

Androecium: Only in disc florets; five stamens fused together around style; anther about 3 mm long and less than one mm wide, anther coloration nearest RHS 17B; filaments fused together, about 2 mm long, filament coloration nearest RHS 2D.

Gynoecium: In ray florets and disc florets, style about 3 mm long and less than 1 mm diameter, split at apical 0.5 mm, style coloration nearest RHS 2D, stigma less than 0.5 mm diameter, stigma coloration nearest RHS 2D.

Involucre: Made of three layers of phyllaries averaging 42 per head; to 3.5 across and 0.5 cm tall.

Phyllaries: Averaging 42 per head, 10 mm long and 3 mm wide.

Phyllaries color: RHS 187A on margin, basal third RHS 145A and darker than RHS 141A in apical half.

Fruit: Achene, pointed at base and rounded at distal end with longitudinal color striations nearest RHS N200A and lighter than RHS 155D; about 4 to 5 mm long and 1.5 mm across.

*Leucanthemum* 'Banana Cream' grows best with adequate moisture but can tolerate some dryness once established. It is tolerant of high temperatures of at least 36° and cold hardy to at least USDA zone 5. Other disease or pest resistance beyond that common to Shasta Daisy has not been observed.

I claim:

1. The new and distinct Shasta Daisy plant, *Leucanthemum* 'Banana Cream' as herein shown and described useful for long-flowering attractive landscaping in borders, in mass, as accent plants, containerized for patio or indoor use, or as a cut flower.

* * * * *